United States Patent [19]

Smith

[11] Patent Number: 5,166,207

[45] Date of Patent: Nov. 24, 1992

[54] METHOD FOR ENHANCING THE SYSTEMIC DELIVERY OF DEXTROMETHORPHAN FOR THE TREATMENT OF NEUROLOGICAL DISORDERS

[75] Inventor: Richard A. Smith, La Jolla, Calif.

[73] Assignee: NeuroTherapeutics, Inc., San Diego, Calif.

[21] Appl. No.: 717,424

[22] Filed: Jun. 17, 1991

[51] Int. Cl.$^5$ ............................................. A61U 31/515
[52] U.S. Cl. ..................................................... 514/270
[58] Field of Search ......................................... 514/270

[56] References Cited

PUBLICATIONS

Chem. Abst. 111-89742z, (1989).

*Primary Examiner*—S. J. Friedman
*Attorney, Agent, or Firm*—Patrick D. Kelly; Frederick W. Pepper

[57] ABSTRACT

A method for enhancing the systemic delivery of dextromethorphan for the treatment of a neurological disorder resulting in injury to nervous tissue, which comprises administering to a patient suffering from the disorder an amount of a cytochrome P450IID6 enzyme inhibitor, sufficient to block dextromethorphan metabolism, and an amount of dextromethorphan sufficient to treat the neurological disorder. Quinidine is particularly suitable for use in the method of the invention.

6 Claims, 1 Drawing Sheet

DOSE-CONCENTRATION RELATIONSHIP

DEXTROMETHORPHAN DOSE (MG/DAY)

METHOD FOR ENHANCING THE SYSTEMIC DELIVERY OF DEXTROMETHORPHAN FOR THE TREATMENT OF NEUROLOGICAL DISORDERS

FIELD OF THE INVENTION

The invention relates to compounds that enhance the delivery of a drug, dextromethorphan, used in the treatment of neurological disorders.

BACKGROUND OF THE INVENTION

It is now known that two common amino acids, glutamate and aspartate, are the major excitatory neurotransmitters in the mammalian brain. It is estimated that between 30 and 40% of all brain neurons use these two agents to communicate. Glutamate and aspartate are referred to as excitatory amino acids (EAA's). After physical trauma or stroke (ischemia), nerve cells which use the EAA's as their neurotransmitters become hyperactive and begin to release very large quantities of the EAA transmitters. This process results in the exhaustion and death of the neurons from EAA overstimulation. The two natural neurotransmitters, glutamate and aspartate, actually become toxins in the injured brain, due to their increased release from neurons. This phenomenon has been termed excitotoxicity.

U.S. Pat. No. 4,806,543 discloses the use of dextrorotatory opiate agonists such as dextrorphan and dextromethorphan to protect against this phenomenon in a number of acute and chronic neurologic disorders, including ischemia, hypoxia, hypoglycemia, epilepsy, Huntington's disease, Alzheimer's disease, and amyotrophic lateral sclerosis (ALS).

Dextromethorphan is known to bind to distinct receptors in the central nervous system (Tortella et al., TIPS 10:501-507, 1989; Craviso and Musacchio, Mol. Pharmacol. 23:629-640, 1983). Although these receptors have not been fully characterized, they may be responsible for the unique anticonvulsant and neuroprotective effects reported for this drug (Leander, Epilepsy Res. 4:28-33, 1989; Koyuncuoglu and Saydam, Intnl. J. Clin. Pharmacol. Ther. Tox. 28:147-152, 1990; Ferkany et al., Eur. J. Pharmacol. 151:151-154, 1988; George et al., Brain Res. 440:35-379, 1988; Choi, Brain Res. 403:333-336, 1987; Goldberg et al., Neurosci. Ltts. 80:11-15, 1987; Prince and Feeser, Neurosci. Ltts. 85:291-296, 1988; Feeser et al., Neurosci. Ltts. 86:340-345, 1988; Steinberg et al., Neurosci. Ltts. 89:193-197, 1988). Additional CNS actions may also arise from the metabolism of dextromethorphan to dextrorphan within the CNS by the cytochrome P450IID6 like enzyme localized in brain tissue (Fonne-Pfister et al., Biochem. Biophys. Res. Commun. 148:1144-1150, 1987; Niznik et al., Arch. Biochem. Biophys. 26:424-432, 1990).

In spite of the potentially desirable CNS activity of dextromethorphan, very little dextromethorphan is capable of reaching the CNS because of its extensive first-pass elimination in humans (Vetticaden et al., Pharmaceut. Res. 6:13-19, 1989; Ramachander et al., J. Pharm. Sci. 66:1047-1048, 1977). Without the administration of massive doses of dextromethorphan (>750 mg/day) on a frequent basis, one cannot hope to overcome the efficient elimination of dextromethorphan in most subjects (Walker and Hunt, Clin. Neuropharmacol. 12:322-330, 1989). As a further complication, one also faces the nonlinearity in dextromethorphan elimination at higher doses. This may make individualization of therapy more difficult and the formation of toxic metabolites and/or adverse drug effects more likely (Walker and Hunt, Clin. Neuropharmacol. 12:322-330, 1989).

The large first-pass elimination of dextromethorphan is accounted for primarily by its O-demethylation to dextrorphan (Vetticaden et al., Pharmaceut. Res. 6:13-19, 1989; Koppel et al., Arzneim.-Forsch. Drug Res. 37:1304-1306, 1987). This metabolite is then rapidly conjugated and eliminated in the urine. The small amounts of dextromethorphan and dextrorphan which reach the CNS are primarily responsible for its antitussive properties. The efficient elimination of dextromethorphan and dextrorphan along with their relatively short half-lives, however, limits their effectiveness and utility for treating neurological disorders.

Accordingly, there is a need for the identification of pharmacologically active compounds that can inhibit the O-demethylation of dextromethorphan to dextrorphan and thereby, preclude the use of excessive dosing with dextromethorphan, with its accompanying problems. Such pharmacologically active compounds can only increase the effectiveness of dextromethorphan and dextrorphan as neuroprotective drugs.

SUMMARY OF THE INVENTION

The present invention provides a method for enhancing the delivery of dextromethorphan for the treatment of a neurological disorder in which excitotoxic mechanisms are implicated. The method involves administering to a patient suffering from the neurological disorder an amount of a cytochrome P450IID6 enzyme inhibitor, sufficient to block the degradation of dextromethorphan, and an amount of dextromethorphan, sufficient to treat a neurological disorder. Quinidine is particularly suitable to enhance delivery of dextromethorphan in the present invention.

BRIEF DESCRIPTION OF THE DRAWING

The drawing is a graph depicting the relationship between dextromethorphan plasma concentrations and dose in patients receiving 150 mg/day of quinidine concurrently.

DETAILED DESCRIPTION OF THE INVENTION

Figure 1:
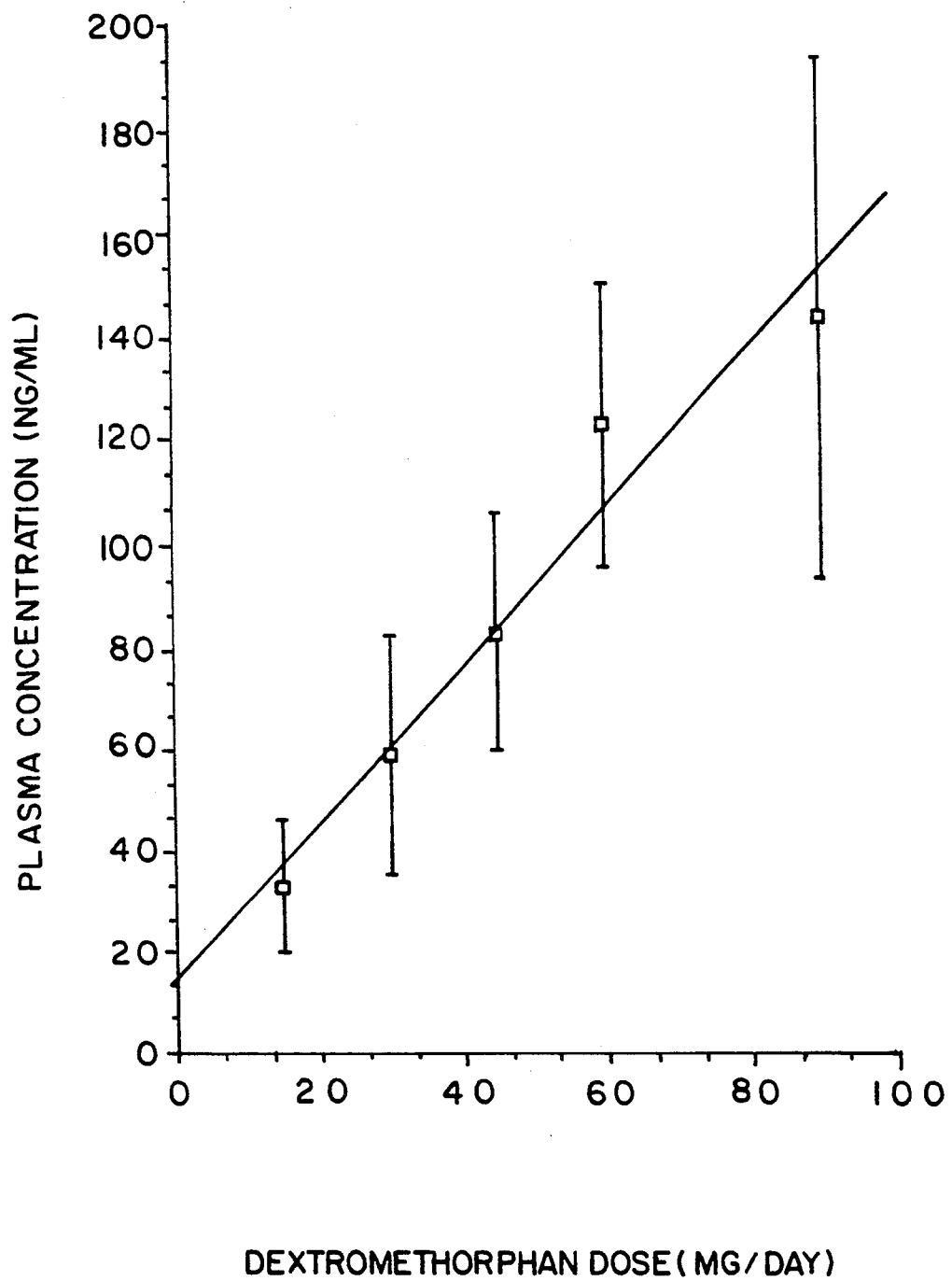

The present invention relates to compounds found to enhance the delivery of dextromethorphan to the CNS for treating neurological disorders. Both dextromethorphan and dextrorphan have neuroprotective effects. The problem is that dextromethorphan is rapidly metabolized to dextrorphan which is eliminated from the body as a sulfate conjugate. The compounds of the present invention inhibit the cytochrome P450IID6 enzyme which is responsible for the O-demethylation of dextromethorphan to dextrorphan. By means of the compounds of the present invention both dextromethorphan and its metabolite, dextrorphan, can reach the CNS without dextromethorphan having to be given in massive amounts.

The preferred compound of the invention is quinidine. Quinidine is a potent and selective inhibitor of the cytochrome P450IID6 enzyme (Brinn et al., Brit. J. Clin. Pharmacol. 22:194-198, 1986; Inaba et al., Brit. J. Clin. Pharmacol. 22:199-200, 1986; Brosen et al., Pharmacol. Tox. 60:312-314, 1987; Otton et al., J. Pharmacol. Exper. Ther. 247:242-248, 1988; Funck-Brentano et al., J. Pharmacol. Exper. Ther. 249:134-142, 1989; Nielsen et al., Br. J. Clin. Pharmacol. 29:299-304, 1990). Quinidine passes the blood brain barrier very poorly (Ochs et al., Amer. Heart J. 100:341-346, 1980; Ochs et al., Clin. Pharmacol. Ther. 38:618-624, 1985) and therefore, will not be present in any significant amount to prevent the O-demethylation of dextromethorphan by the cytochrome P450IID6 like enzyme localized in brain tissue. This creates no problem in dextromethorphan's use since once present in the CNS, dextromethorphan or its metabolite is able to act effectively as a neuroprotective drug.

In addition to quinidine, there are other compounds which may be effective in enhancing the delivery of dextromethorphan by inhibiting the cytochrome P450IID6 enzyme. The compounds can be drawn from the following classes of drugs: anticonvulsants, hypnotics and sedatives, antidepressants, monoamine oxidase inhibitors, antipsychotics, $\beta$-adrenoreceptor blocking drugs, cardiovascular drugs, antimalarials, antihistamines, alkaloids and analgesics. Representative medications in these classes currently demonstrated to exhibit properties of the invention include the following specific compounds: amitriptyline, chlorpromazine, domperidone, haloperidol, haloperidol epoxide, pipamperone, labetalol, metoprolol, oxprenolol, propanolol, timolol, mexiletine, quinine, diphenhydramine, ajmaline, lobeline, fluoxetine hydrochloride, papaverine, yohimbine, and functionally related compounds.

The O-demethylation of dextromethorphan is carried out by the human cytochrome P450IID6 in the liver (Kronbach et al., Anal. Biochem. 162:24-32, 1987; Dayer et al., Clin. Pharmacol. Ther. 45:34-40, 1989). Consequently, individuals lacking the expression of this enzyme eliminate larger quantities of dextromethorphan in their urine and little or minimal amounts of dextrorphan (Guttendorf et al., Ther. Drug Monitor. 10:490-498, 1988; Hildebrand et al., Eur. J. Clin. Pharmacol. 36:315-318, 1989). This information has provided the basis for using the dextromethorphan metabolic ratio of (urinary dextromethorphan/urinary dextrorphan) as a screening tool for identifying subjects with deficiencies in cytochrome P450IID6 expression.

In the present invention, the dextromethorphan metabolic ratio and dextromethorphan plasma level are used to show the inhibition of dextromethorphan O-demethylation by quinidine with the resulting increase in dextromethorphan levels. The metabolic ratio of dextromethorphan is determined by using the following equation:

$$MR = \frac{\text{Molar Dextromethorphan amount in 12 hour urine}}{\text{Molar Dextrorphan amount in 12 hour urine}}$$

A metabolic ratio <0.30 indicates extensive metabolism.

Both dextromethorphan plasma levels, with and without quinidine, and dextromethorphan and dextrorphan urinary levels without quinidine were determined using an HPLC assay with fluorescence detection. Dextromethorphan and dextrorphan urinary levels with quinidine were determined using a gas chromatographic-mass spectroscopy (gc-ms) assay.

The method of the invention is carried out by administering to a patient suffering from a neurological disorder an amount of a cytochrome P450IID6 enzyme inhibitor such as quinidine, sufficient to block dextromethorphan metabolism, and an amount of dextromethorphan, sufficient to treat neurological disorders. The method is suitable for use in any animal species having a cytochrome P450IID6 like enzyme.

Administration can be by any technique capable of introducing a compound of the invention such as quinidine and dextromethorphan into the blood stream of a patient, including oral administration and intravenous, intramuscular, and subcutaneous injections. For stroke or head trauma, the preferred method of administration is intravenous. Oral administration is the preferred method for epilepsy and neurodegenerative diseases.

Typical doses in orally acceptable pharmaceutical carriers would be from 30 to 300 mg, preferably from 50 to 150 mg, for dextromethorphan, and from 50 to 500 mg, preferably from 50 to 150 mg, for compounds of the invention such as quinidine. These doses are for administration to a typical 70 kg human. Administration can be adjusted to provide the same relative dose per unit of body weight.

A preferred formulation comprises dextromethorphan, quinidine, and an inert carrier suitable for use as an injectable solution or suspension. Aqueous solutions, optionally containing minor amounts of an organic solvent, such as ethanol, for use in increasing solubility, are particularly preferred. Preferred is an injectable solution containing from 30 to 300 mg, preferably from 50 to 150 mg, of dextromethorphan, and from 50 to 500 mg, preferably from 50 to 150 mg, for compounds of the invention such as quinidine. The amount utilized for any particular patient will vary depending on the body weight and particular use, as is well understood in the art. Typical concentrations in the blood stream on the order of 100 to 1000 ng/mL, preferably 250 to 500 ng/mL, for dextromethorphan and on the order of 1 to 7 mcg/mL, preferably 3 to 5 mcg/mL, for quinidine will be useful.

Injectable formulations of the invention will differ from simple aqueous solutions in that they have been formulated for pharmaceutical use and therefore, will not contain pyrogens and other substances that may be present in typical laboratory solutions of organic compounds.

The following example is provided for the purpose of illustration only and is not to be considered limiting of the invention unless otherwise specified.

EXAMPLE

Dextromethorphan and dextrorphan urinary levels without quinidine were determined by the following procedure. For this determination, 40 mg. of thebaine was added as an internal standard to 1 mL of urine. To this was added 2000 units of beta-glucuronidase in 1 mL of acetate buffer (0.1M, pH 5.0). The mixture was incubated for 18 hours at 37° C. and then extracted by adding 1 mL of phosphate buffer (pH 12, 0.10M) and 7 mL of n-butanol/hexane (10:90 v/v). After mixing and centrifugation, the organic layer was transferred to a clean tube, acidified with 400 $\mu$L of 0.01N HCl and 20 $\mu$L of the aqueous phase injected into the HPLC system. The HPLC consisted of a phenyl column equilibrated with a mobile phase of acetonitrile: water containing 10 mm/L KHP$_4$, 10 mm/L hexane sulfonic acid, pH 4.0 (51:49, v/v; flow rate 1.2 mL/min). Detection of thebaine, dextromethorphan and dextrorphan was achieved by fluorescence (Kratos FS-980 Fluorometer) with an excitation wavelength of 228 nm and no emission cutoff filter.

The above procedure with slight modification was used to determine dextromethorphan plasma levels.

A gc-ms assay was employed for determining dextromethorphan and dextrorphan levels in the presence of quinidine. Briefly, 0.5 ml urine samples were spiked with 500 ng of dimethacrine. The urine pH was adjusted to 5.0 with 1 ml of 0.1M acetate buffer followed by β-glucuronidase (2000 units/ml urine). The mixture was incubated and shaken at 37° C. for 18 hours. The urine was subsequently adjusted to pH 10–11 with 1.0 mL of phosphate buffer and the urine extracted with 5 mL of dichloromethane. The dichloromethane extract was then evaporated under nitrogen, reconstituted in 300 μL of BSTFA and injected onto the gc-ms equipped with a capillary SE-30 column. Gas chromatographic conditions were: injector and transfer line temperature 250° C., oven 70° C. to 260° C. at 20° C. per minute, and source temperature 180° C. Detection was by selected ion monitoring at m/z 271 for dextromethorphan, 294 for the internal standard, and 329 for dextrorphan. Typical standard curves for dextromethorphan and dextrorphan were provided. Assay sensitivity was 100 ng/ml for dextromethorphan and 400 ng/ml for dextrorphan.

It is shown in Table I below that quinidine is an extremely potent inhibitor of dextromethorphan O-demethylation in humans. As shown in Table I, six patients suffering from ALS were administered orally a single 60 mg dextromethorphan dose in the presence and absence of an oral administration of 150 mg of quinidine. This resulted in a substantial increase of the dextromethorphan metabolic ratio (urinary dextromethorphan/urinary dextrorphan). The metabolic ratio was increased substantially as shown in Table I below.

TABLE I

Effect of 150 mg/day of quinidine on the dextromethorphan metabolic ratio in ALS patients

| PATIENT | DEXTRO-METHORPHAN DOSE (MG) | DEXTRO-METHORPHAN METABOLIC RATIO | QUINIDINE DOSE (MG/DAY) |
|---|---|---|---|
| 1 | 60 | 0.0048 | 0 |
| 1 | 60 | 4.090 | 150 |
| 2 | 60 | 0.0220 | 0 |
| 2 | 60 | 3.460 | 150 |
| 3 | 60 | 0.0002 | 0 |
| 3 | 60 | 0.635 | 150 |
| 4 | 60 | 0.0003 | 0 |
| 4 | 60 | 0.420 | 150 |
| 5 | 60 | <0.0002 | 0 |
| 5 | 60 | 0.631 | 150 |
| 6 | 60 | 0.054 | 0 |
| 6 | 60 | 3.29 | 150 |

Concurrent analysis of plasma dextromethorphan levels have also shown the 10–12 hour post dosage level to be elevated considerably by quinidine. Thus, the chronic administration of 120 mg of dextromethorphan per day for one week resulted in extremely low plasma levels of dextromethorphan or levels which were less than 5 ng/ml. However, as shown in Table II below, treatment with 150 mg of quinidine resulted in dextromethorphan plasma levels which ranged from 28–46 ng/ml 10–12 hours after a single 60 mg dose of dextromethorphan.

TABLE II

The effect of 150 mg/day of quinidine on plasma dextromethorphan levels

| PA-TIENT | DEXTRO-METHORPHAN DOSE (MG) | DEXTRO-METHORPHAN PLASMA LEVEL | QUINIDINE DOSE (MG/DAY) |
|---|---|---|---|
| 1 | 120 MG/DAY | NOT DECTECTABLE | 0 |
| 1 | 60 MG ONCE | 33 NG/ML | 150 |
| 2 | 120 MG/DAY | 9.3 NG/ML | 0 |
| 2 | 60 MG ONCE | 29.7 NG/ML | 150 |
| 3 | 120 MG/DAY | NOT DECTECTABLE | 0 |
| 3 | 60 MG ONCE | 29.0 NG/ML | 150 |
| 4 | 120 MG/DAY | 16.5 NG/ML | 0 |
| 4 | 60 MG ONCE | 28.8 NG/ML | 150 |
| 5 | 120 MG/DAY | 6.05 NG/ML | 0 |
| 5 | 60 MG ONCE | 45.6 NG/ML | 150 |

Additional studies have also been carried out to better define the dose response profile of dextromethorphan in the presence of quinidine. This work as shown in the drawing shows that dextromethorphan plasma levels are increased substantially by the co-administration of 150 mg of quinidine per day. Such an increase in dextromethorphan plasma levels provides support for the enhanced CNS delivery of dextromethorphan with coadministration of quinidine. Furthermore, as the normal dose of quinidine for antiarrhythmic action is 600–1200 mg/day, the use of quinidine for enhanced delivery of dextromethorphan requires quinidine doses far below those typically employed for therapeutic action.

The invention now being fully described, it will be apparent to one of ordinary skill in the art that many changes and modifications can be made thereto without departing from the spirit or scope of the appended claims.

What is claimed is:

1. A method for enhancing the systemic delivery of dextromethorphan for the treatment of a neurological disorder resulting in injury to nervous tissue, which comprises:

administering to a patient suffering from said neurological disorder an amount of a cytochrome P450IID6 enzyme inhibitor, sufficient to block dextromethorphan metabolism, and an amount of dextromethorphan, sufficient to treat said neurological disorder.

2. The method of claim 1, wherein said inhibitor is quinidine.

3. The method of claim 1, wherein said neurological disorder results from ischemia, hypoxia, hypoglycemia, epilepsy, Huntington's disease, Alzheimer's disease, or amyotrophic lateral sclerosis.

4. A method for enhancing the systemic delivery of dextromethorphan for the treatment of a neurological disorder mediated by an endogenous excitatory amino acid, which comprises:

administering to a patient suffering from said neurological disorder an amount of a cytochrome P450IID6 enzyme inhibitor, sufficient to block dextromethorphan metabolism, and an amount of dextromethorphan, sufficient to treat said neurological disorder.

5. The method of claim 4, wherein said inhibitor is quinidine.

6. The method of claim 4, wherein said neurological disorder results from ischemia, hypoxia, hypoglycemia, epilepsy, Huntington's disease, Alzheimer's disease, or amyotrophic lateral sclerosis.

* * * * *